United States Patent
Komuro et al.

(10) Patent No.: US 10,603,125 B2
(45) Date of Patent: Mar. 31, 2020

(54) MEDICAL MANIPULATOR

(71) Applicant: OLYMPUS CORPORATION, Tokyo (JP)

(72) Inventors: Takahiro Komuro, Tokyo (JP); Ryuichi Yorimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 322 days.

(21) Appl. No.: 15/819,617

(22) Filed: Nov. 21, 2017

(65) Prior Publication Data

US 2018/0085178 A1 Mar. 29, 2018

Related U.S. Application Data

(63) Continuation of application No. PCT/JP2016/065885, filed on May 30, 2016.

(30) Foreign Application Priority Data

Jun. 1, 2015 (JP) ................. 2015-111329

(51) Int. Cl.
*G05B 15/00* (2006.01)
*G05B 19/00* (2006.01)
(Continued)

(52) U.S. Cl.
CPC .............. *A61B 34/35* (2016.02); *A61B 34/37* (2016.02); *A61B 34/71* (2016.02); *A61B 34/77* (2016.02);
(Continued)

(58) Field of Classification Search
None
See application file for complete search history.

(56) References Cited

U.S. PATENT DOCUMENTS

| 7,524,320 | B2 | 4/2009 | Tierney et al. |
| 7,963,913 | B2 | 6/2011 | Devengenzo et al. |
| | | (Continued) | |

FOREIGN PATENT DOCUMENTS

| JP | 2004-105451 A | 4/2004 |
| WO | 2010/126127 A1 | 11/2010 |
| | (Continued) | |

OTHER PUBLICATIONS

Extended Supplementary European Search Report dated Jan. 3, 2019 in European Patent Application No. 16 80 3303.3.
(Continued)

*Primary Examiner* — Bhavesh V Amin
(74) *Attorney, Agent, or Firm* — Scully, Scott, Murphy & Presser, P.C.

(57) ABSTRACT

A medical manipulator having: a first rotatable body configured to be rotated about a rotation axis to exert a driving force transmitted by a wire to drive at least one of an elongated portion and an end effector; and a second rotatable body configured to be detachably coupled to the first rotatable body, wherein the second rotatable body is operatively connected to an actuator to be rotated by the actuator, wherein a shape of the first rotatable body corresponds to a shape of the second rotatable body such that as the first rotatable body and the second rotatable body are brought into contact with each other, a pressing force with which the first rotatable body is pressed against the second rotatable body is converted into a rotational force of the second rotatable body to rotate the second rotatable body into a predetermined alignment with the first rotatable body.

6 Claims, 15 Drawing Sheets

(51) Int. Cl.
   *A61B 34/35*   (2016.01)
   *A61B 34/37*   (2016.01)
   *A61B 34/00*   (2016.01)
   *B25J 3/00*   (2006.01)
   *B25J 9/16*   (2006.01)
   *A61B 17/00*   (2006.01)
   *A61B 34/30*   (2016.01)
   *A61B 90/00*   (2016.01)
   *A61B 90/90*   (2016.01)

(52) U.S. Cl.
   CPC ............... *B25J 3/00* (2013.01); *B25J 9/1689* (2013.01); *A61B 90/90* (2016.02); *A61B 2017/00477* (2013.01); *A61B 2034/301* (2016.02); *A61B 2090/065* (2016.02); *A61B 2090/066* (2016.02); *A61B 2090/0811* (2016.02); *Y10S 901/41* (2013.01)

(56) References Cited

U.S. PATENT DOCUMENTS

| | | |
|---|---|---|
| 2002/0087049 A1 | 7/2002 | Brock et al. |
| 2004/0049205 A1 | 3/2004 | Lee et al. |
| 2004/0092912 A1 | 5/2004 | Jinno et al. |
| 2011/0015650 A1 | 1/2011 | Choi et al. |
| 2014/0148821 A1 | 5/2014 | Nakayama |

FOREIGN PATENT DOCUMENTS

| | | |
|---|---|---|
| WO | WO 2010/126127 A1 | 11/2010 |
| WO | 2011/037394 A2 | 3/2011 |

OTHER PUBLICATIONS

International Search Report dated Aug. 16, 2016 received in PCT/JP2016/065885.

MEDICAL MANIPULATOR

CROSS-REFERENCE TO RELATED APPLICATIONS

This application is a continuation application based on a PCT International Application No. PCT/JP2016/065885, filed on May 30, 2016, whose priority is claimed on Japanese Patent Application No. 2015-111329, filed Jun. 1, 2015. Both of the content of the PCT International Application and the Japanese Application are incorporated herein by reference.

BACKGROUND

Related Field

The present disclosure relates to a medical manipulator.

Description of Related Art

Conventionally, surgery using a remote operation in which a treatment tool is inserted into a treatment target portion in a body and the treatment tool is operated from outside of the body is known. Further, a medical manipulator for performing a medical practice such as surgery by a remote operation is known (refer to, for example, U.S. Pat. No. 7,963,913, U.S. Pat. No. 7,524,320, and PCT International Patent Publication No. 2010/126127).

For example, in each of medical manipulators disclosed in U.S. Pat. No. 7,963,913, U.S. Pat. No. 7,524,320, and PCT International Application Publication No. WO 2010/126127, a clean area which is directly in contact with an inside of a patient's body and an unclean area which is not in contact with the patient are set, and a device existing in the clean area and a device existing in the unclean area can be separably installed therein. In each of the medical manipulators disclosed in U.S. Pat. No. 7,963,913, U.S. Pat. No. 7,524,320, and PCT International Application Publication No. WO 2010/126127, a power transmission path for operating an end effector disposed in the clean area can be separated between the clean area and the unclean area

SUMMARY

A medical manipulator comprising: an elongated portion and an end effector coupled to the elongated portion, wherein at least one of the elongated portion and the end effector are configured to be driven to change a position and/or an orientation; a wire, wherein a distal end of the wire is operatively connected to the at least one of the elongated portion and the end effector to transmit a driving force to drive the at least one of the elongated portion and the end effector; a first rotatable body operatively connected to a proximal end of the wire, wherein the first rotatable body is configured to be rotated about a rotation axis to exert the driving force transmitted by the wire to drive the at least one of the elongated portion and the end effector; and a second rotatable body configured to be detachably coupled to the first rotatable body, wherein the second rotatable body is operatively connected to an actuator to be rotated by the actuator, wherein a shape of the first rotatable body corresponds to a shape of the second rotatable body such that as the first rotatable body and the second rotatable body are brought into contact with each other, a pressing force with which the first rotatable body is pressed against the second rotatable body is converted into a rotational force of the second rotatable body to rotate the second rotatable body into a predetermined alignment with the first rotatable body.

DETAILED DESCRIPTION

First Embodiment

Figure 1:
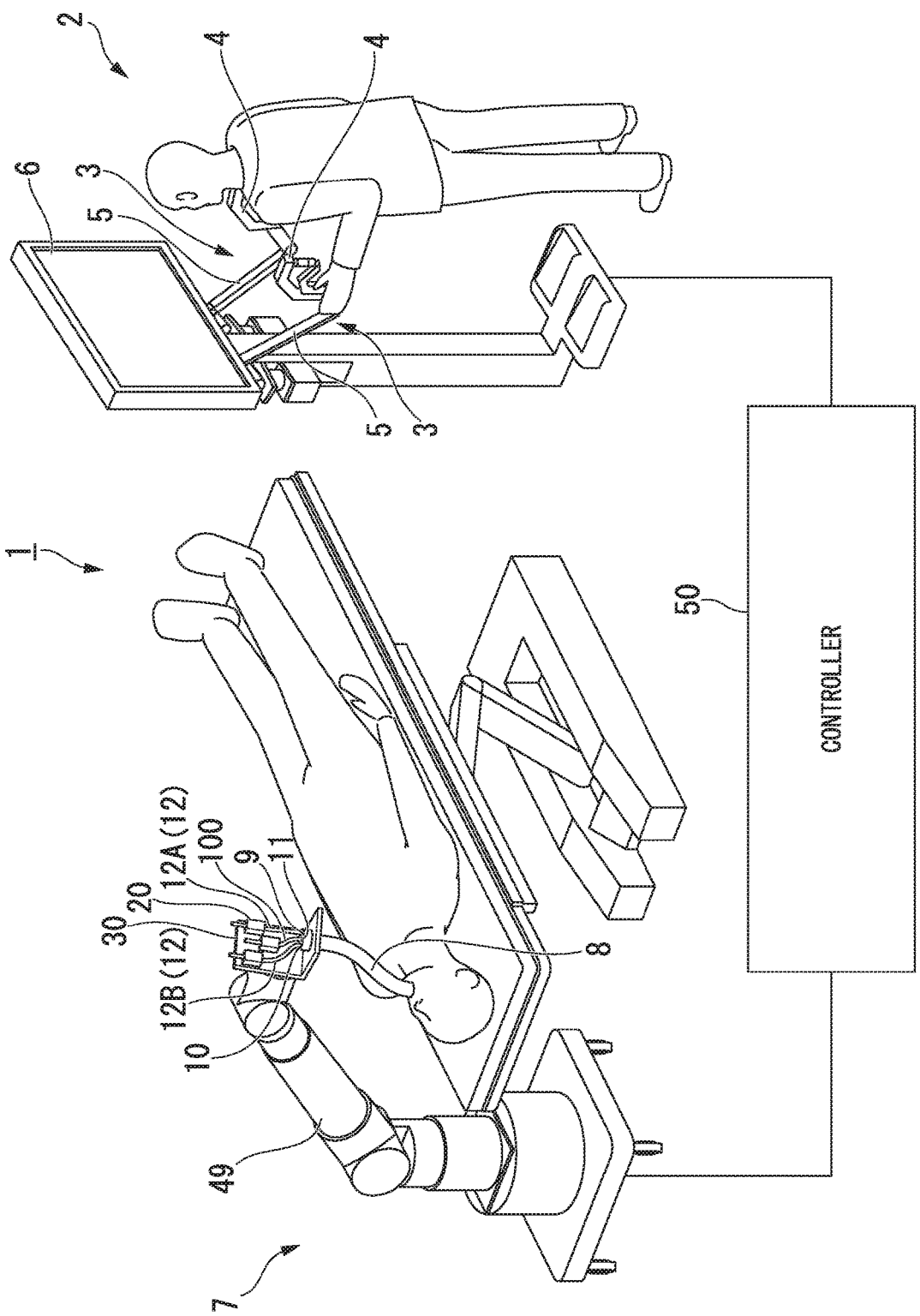
FIG. 1 is an overall view illustrating a medical manipulator according to a first embodiment.
Figure 2:
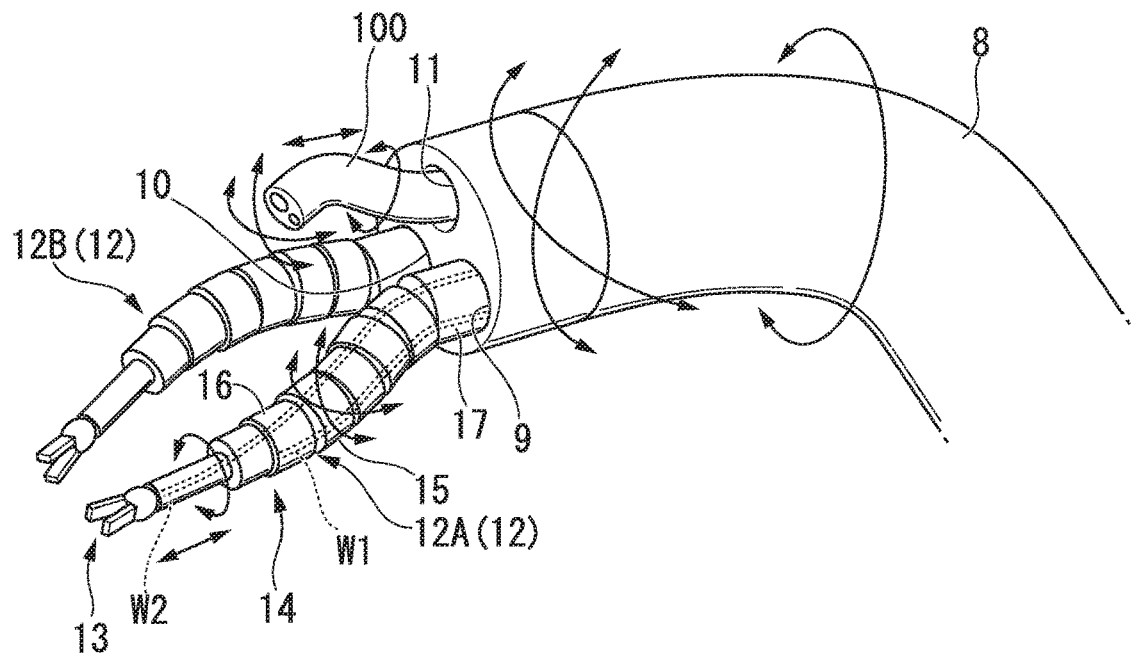
FIG. 2 is a perspective view illustrating a part of the medical manipulator according to the first embodiment.
Figure 3:
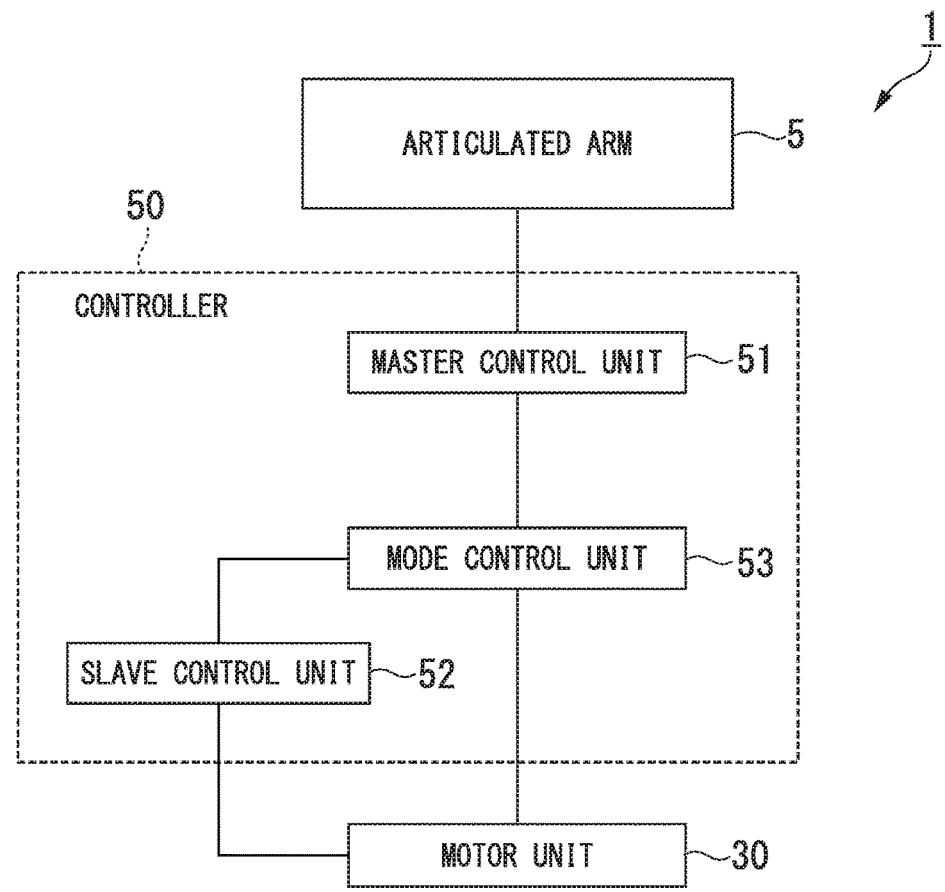
FIG. 3 is a block diagram illustrating the medical manipulator according to the first embodiment.
Figure 4:
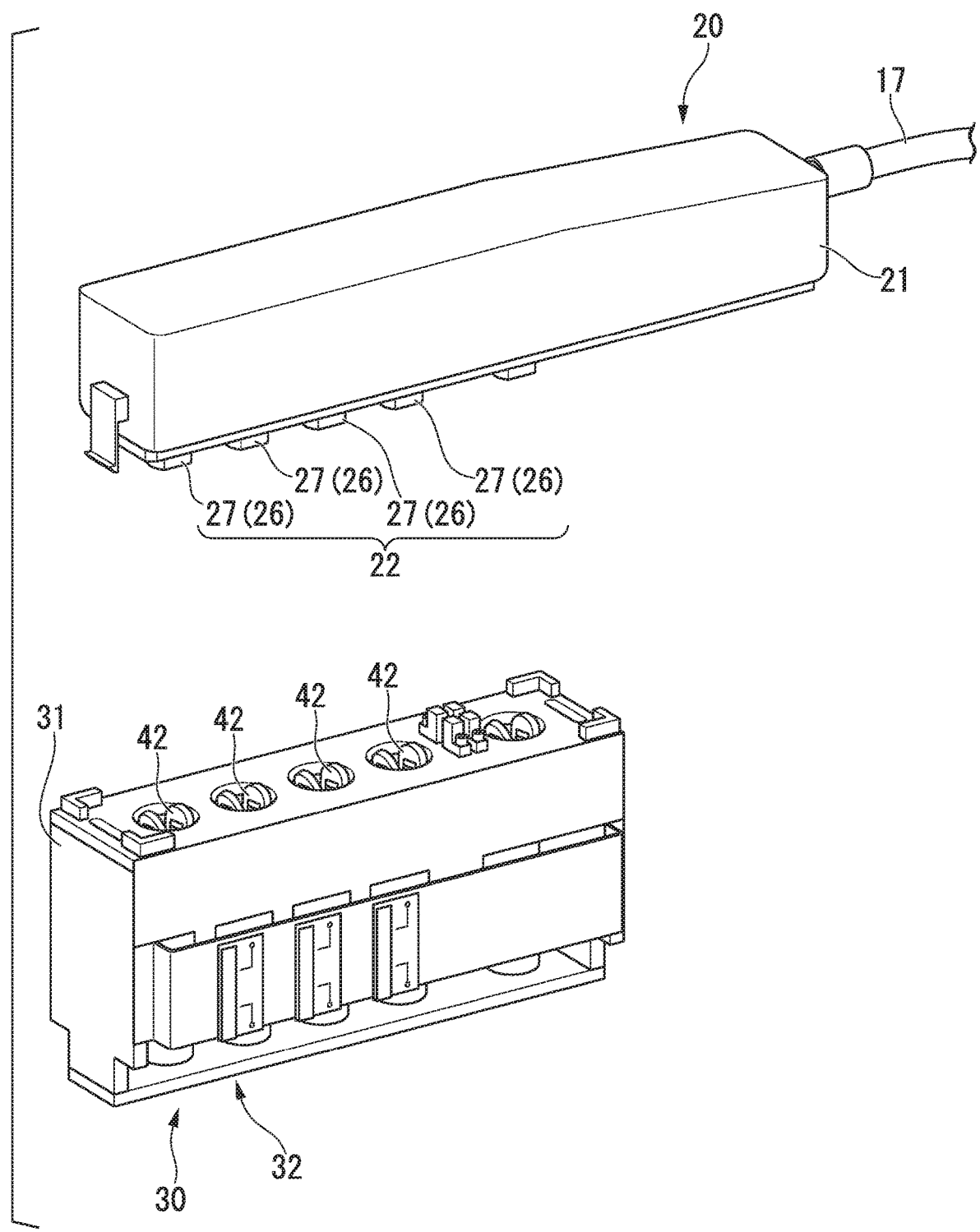
FIG. 4 is a perspective view illustrating a part of the medical manipulator according to the first embodiment.
Figure 5:
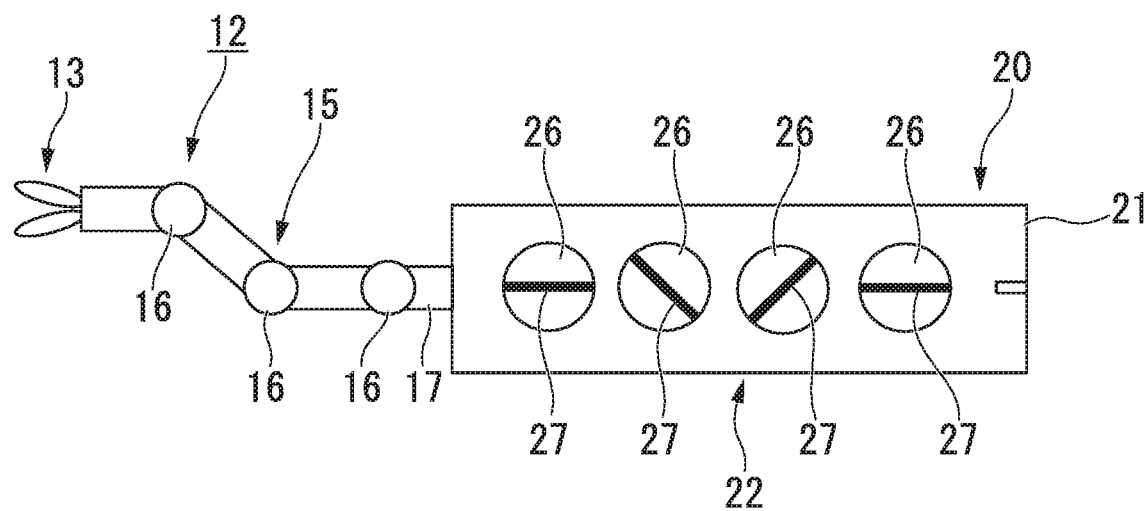
FIG. 5 is a schematic view illustrating a treatment tool of the medical manipulator according to the first embodiment.
Figure 6:
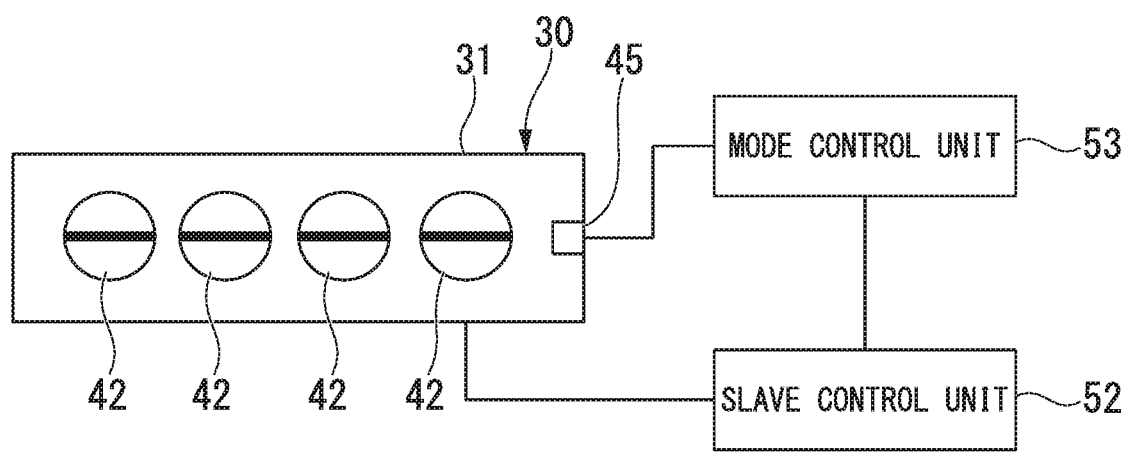
FIG. 6 is a schematic view illustrating a motor unit of the medical manipulator according to the first embodiment.
Figure 7:
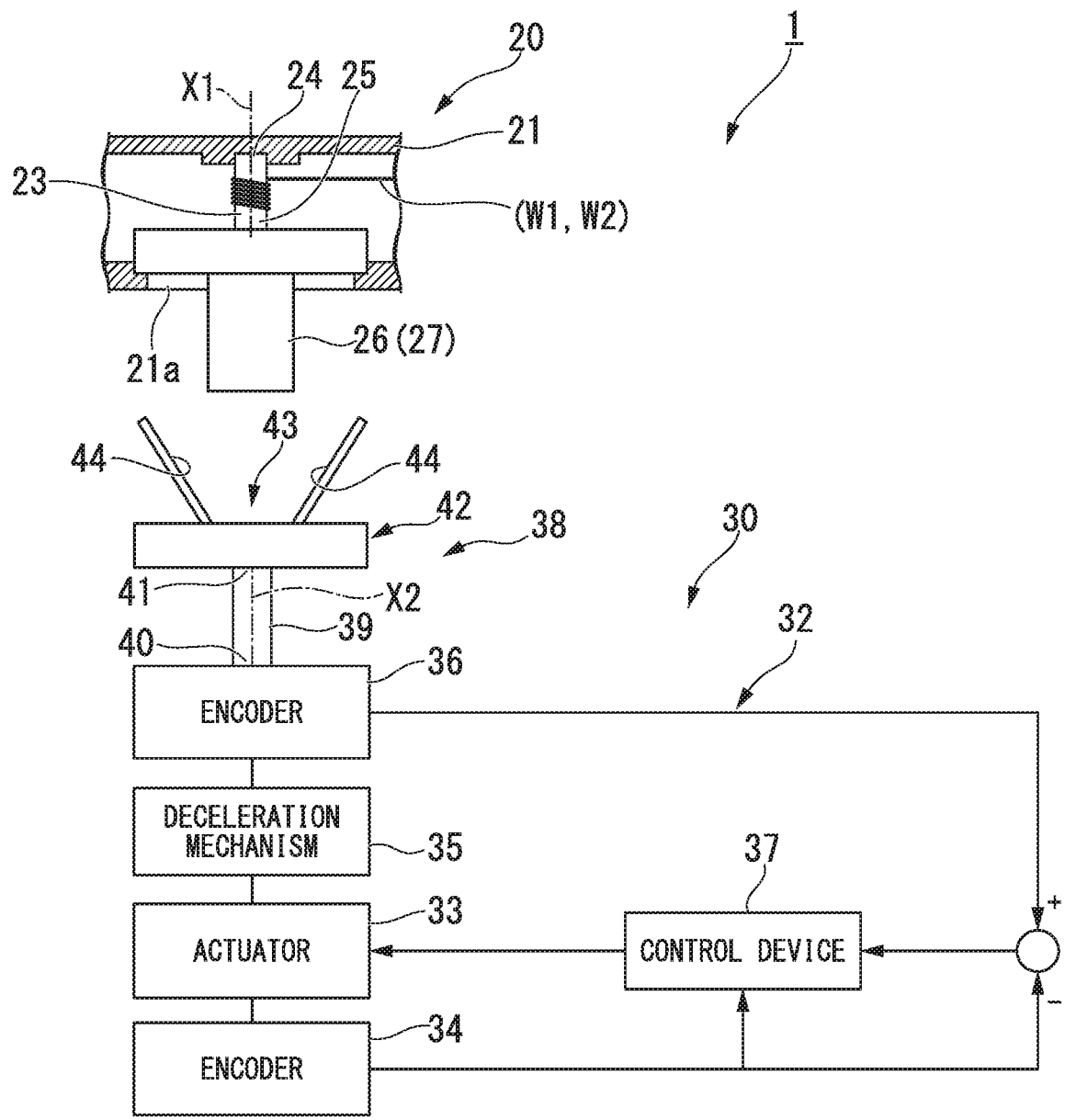
FIG. 7 is a conceptual diagram of an internal structure of the motor unit of the medical manipulator according to the first embodiment.
Figure 8:
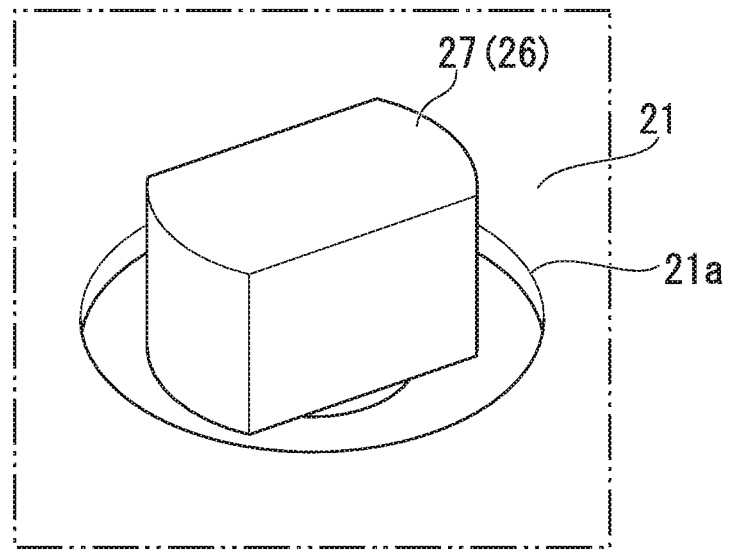
FIG. 8 is a perspective view illustrating a protruding portion provided at a first transmission unit of the treatment tool of the medical manipulator according to the first embodiment.
Figure 9:
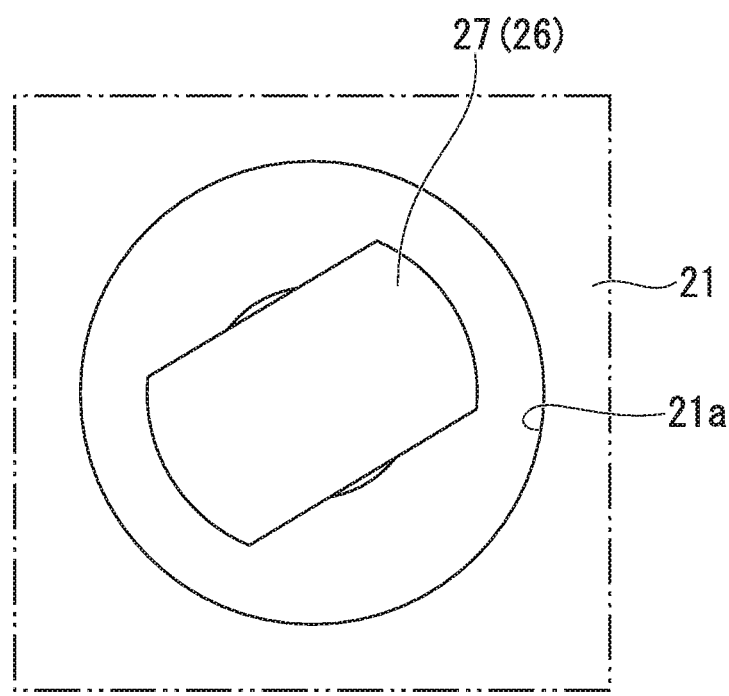
FIG. 9 is a plan view illustrating the protruding portion provided at a first transmission unit of the treatment tool of the medical manipulator according to the first embodiment.
Figure 10:
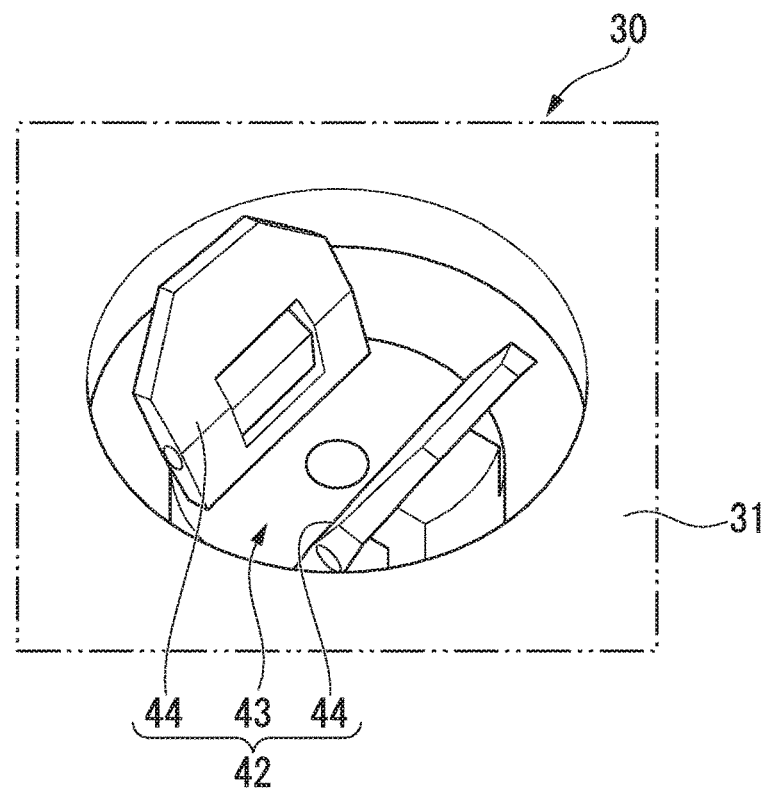
FIG. 10 is a perspective view illustrating an engaged portion provided in a second transmission unit of the motor unit of the medical manipulator according to the first embodiment.
Figure 11:
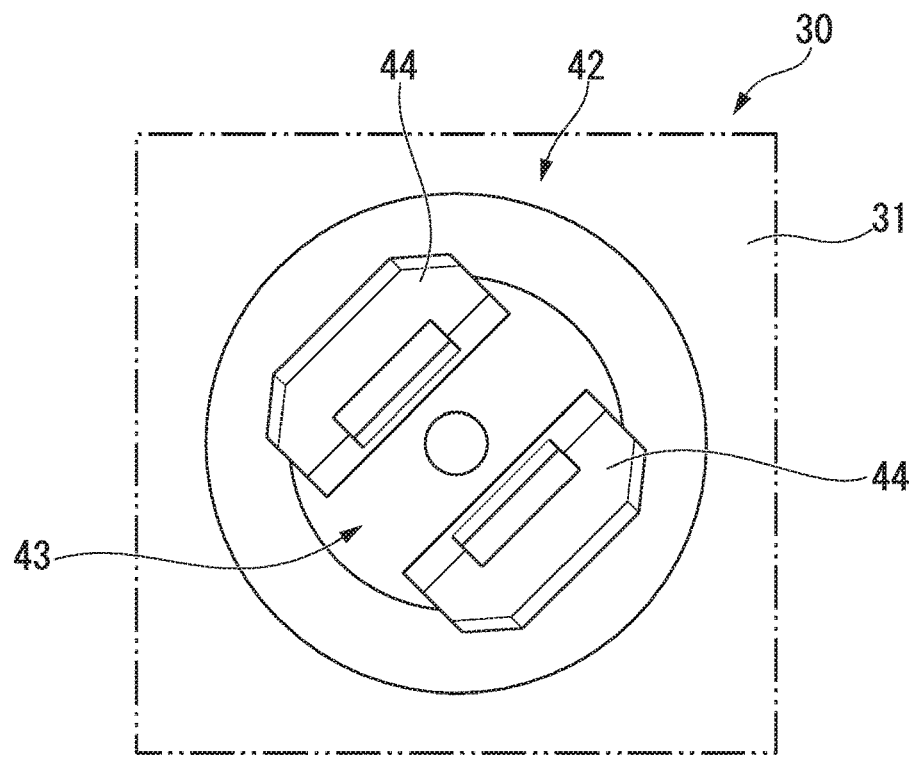
FIG. 11 is a plan view illustrating the engaged portion provided in a second transmission unit of the motor unit of the medical manipulator according to the first embodiment.

A first embodiment of a medical manipulator will be described. FIG. 1 is an overall view illustrating the medical manipulator. FIG. 2 is a perspective view illustrating a part of the medical manipulator. FIG. 3 is a block diagram illustrating the medical manipulator. FIG. 4 is a perspective view illustrating part of the medical manipulator. FIG. 5 is a schematic view illustrating a treatment tool of the medical manipulator. FIG. 6 is a schematic view illustrating a motor unit of the medical manipulator. FIG. 7 is a conceptual diagram of an internal structure of the motor unit of the medical manipulator. FIG. 8 is a perspective view illustrating a protruding portion provided at a first transmission unit of the treatment tool of the medical manipulator. FIG. 9 is a plan view illustrating the protruding portion provided at a first transmission unit of the treatment tool of the medical manipulator. FIG. 10 is a perspective view illustrating an engaged portion provided in a second transmission unit of the motor unit of the medical manipulator. FIG. 11 is a plan view illustrating the engaged portion provided in a second transmission unit of the motor unit of the medical manipulator.

As illustrated in FIG. 1, a medical manipulator 1 includes a master manipulator 2, a slave manipulator 7 and a controller 50 (a control unit).

The master manipulator 2 includes a master arm 3 and a display unit 6.

The master arm 3 is provided to operate a medical instrument such as a treatment tool 12 and an endoscope 100 to be described later from an outside of the body. For example, the master arm 3 of the embodiment serves as an operation unit which provides an instruction to operate the treatment tool 12. The master arm 3 is connected to a master control unit 51 which will be described later and is provided at the controller 50. The master arm 3 has a grip portion 4 and an articulated arm 5.

The grip portion 4 is provided at an end of the master arm 3 to allow an operator to grip and operate the master arm 3.

The articulated arm 5 has at least one degree of freedom by having a plurality of joints. The articulated arm 5 has a plurality of encoders which are not illustrated and detect a position and a posture of the grip portion 4. A motion in which the operator grips the grip portion 4 of the master arm 3 and moves the articulated arm 5 is converted into information necessary to operate the treatment tool 12, the endoscope 100 or the like by each of the encoders. Also, an arrangement of the plurality of joints of the articulated arm 5 may be the same as that of the treatment tool 12, that is, may have a similar relationship thereto. In this case, since a motion in which each of the joints of the articulated arm 5 moves is reflected in an operation of the treatment tool 12, the operator can perform an intuitive operation.

The display unit 6 is provided to display an image captured by the endoscope 100 which will be described later, information necessary to operate the medical manipulator 1 according to the embodiment or the like. The display unit 6 is connected to the controller 50. For example, the display unit 6 displays an image based on a video signal output from the controller 50. A constitution of the display unit 6 is not particularly limited.

The slave manipulator 7 has a medical overtube 8, the treatment tool 12, a motor unit 30 and a slave arm 49.

As illustrated in FIGS. 1 and 2, the medical overtube 8 has a first lumen 9 and a second lumen 10 for installing the treatment tool 12 and a third lumen 11 for installing the endoscope 100. The medical overtube 8 has a tubular shape which can be inserted into a digestive tract or the like from a natural opening such as a patient's mouth. Further, if necessary, the medical overtube 8 may perform a bending motion in response to an operation outside the body. Furthermore, the medical overtube 8 is not limited to the above-described constitution. For example, the medical overtube 8 may have a constitution in which the treatment tool 12 is fixed to the medical overtube 8 in a state in which the treatment tool 12 protrudes from a tip end of the medical overtube 8.

The treatment tool 12 is a manipulator for performing treatment on a treatment target portion in the body according to an operation from an outside of the body. The treatment tool 12 can be inserted into the first lumen 9 or the second lumen 10 of the medical overtube 8. In the embodiment, the treatment tool 12 has a first treatment tool 12A which is insertable into the first lumen 9 and a second treatment tool 12B which is insertable into the second lumen 10. Also, the medical manipulator according to the embodiment is not limited to having two treatment tools 12 but may have only one treatment tool 12 or three or more treatment tools 12.

In the embodiment, the first treatment tool 12A and the second treatment tool 12B have constitutions for performing the treatment such as incision, grip, suture or the like on the treatment target portion in the body. A constitution of the first treatment tool 12A and a constitution of the second treatment tool 12B may be the same as each other or may be different from each other. Hereinafter, the constitution of the first treatment tool 12A of the two treatment tools 12 will be described, and the description of the second treatment tool 12B will be omitted.

The first treatment tool 12A (hereinafter simply referred to as "treatment tool 12") has an end effector 13, an elongated portion 14, and a first base end portion 20.

The end effector 13 is provided at the tip end of the treatment tool 12 to perform the treatment on the treatment target portion in the body.

A constitution of the end effector 13 is not particularly limited as long as it is a treatment unit working on the treatment target portion. For example, the end effector 13 may be a device, such as a grasping forceps, an incision knife or an electrode, which performs a surgical treatment on tissues in the body, or may be an optical or ultrasonic observation device for observing the inside of the body. For example, the end effector 13 may be the grasping forceps having a pair of jaws capable of being opened and closed according to a pulling operation by a drive wire W2 or the knife for incising the tissues by applying a high frequency current.

The elongated portion 14 is an elongated flexible member which is inserted into the body to guide the end effector 13 to the treatment target portion in the body. In the embodiment, the elongated portion 14 has flexibility as a whole. The elongated portion 14 having the flexibility can guide the end effector 13 from the natural opening such as the mouth to the treatment target portion along a route of the digestive tract and the like via the digestive tract and the like.

Further, the elongated portion 14 may have the flexibility or may be a hard member which has a substantially linear shape. Hereinafter, an example of a constitution of the elongated portion 14 having the flexibility is shown.

The elongated portion 14 having the flexibility has a joint portion 15 and a flexible tube portion 17.

The joint portion 15 has a plurality of joint elements 16 which are arranged in a center line direction of the elongated portion 14 and connected to each other and thus can be entirely bent and deformed. An angle wire W1 which transmits an amount of a force for bending and deforming the joint portion 15 from the first base end portion 20 side is connected to the joint element 16 closest to the tip end of the joint portion 15.

The flexible tube portion 17 is a tubular member having the flexibility which can have a curved shape similar to that of the first lumen 9 or the second lumen 10 when the medical overtube 8 is in a curved state. The angle wire W1 for bending and deforming the joint portion 15 and the drive wire W2 for operating the end effector 13 are inserted into the flexible tube portion 17.

As illustrated in FIGS. 4, 5 and 7, the first base end portion 20 has a first housing 21 and a first transmission unit 22.

The first housing 21 is fixed to a base end of the flexible tube portion 17. An inside of the first housing 21 communicates with an inside of the flexible tube portion 17. A base end of the above-described drive wire W2 or angle wire W1 disposed in the flexible tube portion 17 is disposed in the first housing 21. The first housing 21 has an opening 21a (refer to FIG. 7) which is capable of exposing a protruding portion 26, which will be described later, to an outside.

The first transmission unit 22 has a first rotating body 23 and the protruding portion 26.

As illustrated in FIG. 7, the first rotating body 23 is a bar-shaped member on which the base end of the angle wire W1 or the base end of the drive wire W2 is wound. A number of first rotating bodies 23 corresponding to the number of drive wires W2 and angle wires W1 are provided in the first housing 21. The first rotating body 23 is connected to the first housing 21 to be rotatable about a predetermined rotation center X1. Further, in a state in which the first base end portion 20 deviates from a motor unit 30 (a second base end portion) which will be described later, the first rotating body 23 has a rotational resistance force which resists the pulling force transmitted from the angle wire W1, the drive wire W2 or the like and does not rotate within the first housing 21. For example, the first rotating body 23 may be capable of rotating with respect to the first housing 21 with a frictional force of a predetermined magnitude with respect to the first housing 21 as the rotational resistance force.

In the first rotating body 23 of the embodiment, for example, a center line of the first rotating body 23 is the predetermined rotation center X1 of the rotating body 23. Also, a first end 24 of both ends 24 and 25 of the first rotating body 23 in the center line direction is connected to the first housing 21 to be rotatable with respect to the first housing 21.

The protruding portion 26 illustrated in FIGS. 7 to 9 is provided at a second end 25 of both ends of the first rotating body 23 in the center line direction illustrated in FIG. 7 which is opposite to the first end 24. The protruding portion 26 is exposed to an outside of the first housing 21 from the opening 21a of the first housing 21. Also, if an engaged portion 42 which will be described later can be engaged with the protruding portion 26 through the opening 21a of the first housing 21, the protruding portion 26 may protrude from the opening 21a or may not protrude from the opening 21a but may be located inside the first housing 21. The protruding portion 26 is integrally rotatable with the first rotating body 23 about the predetermined rotation center X1 (the center line of the first rotating body 23 in the embodiment) in the first rotating body 23. In the embodiment, the protruding portion 26 and the first rotating body 23 are integrally molded. Also, the protruding portion 26 and the first rotating body 23 may be separate bodies and may be connected to each other.

The protruding portion 26 in the embodiment has an engaging thread portion 27 which is long in a direction orthogonal to the predetermined rotation center X1 of the first rotating body 23. The engaging thread portion 27 has a shape based on a shape of the engaged portion 42 to be engaged with the engaged portion 42 when in a predetermined positional relationship with the engaged portion 42.

As illustrated in FIGS. 4, 6 and 7, the motor unit 30 can be installed on and separated from the proximal end side of the treatment tool 12 as a second base end portion which can be installed on and separated from the first base end 20.

The motor unit 30 includes a second housing 31, a drive unit 32, a second transmission unit 38 and a treatment tool installation sensor 45.

The second housing 31 has a container shape in which the second transmission unit 38 and the drive unit 32 are accommodated. The second housing 31 can be installed on and separated from the first housing 21, for example, manually.

As illustrated in FIG. 7, the drive unit 32 includes an actuator 33, a first encoder 34, a deceleration mechanism 35, a second encoder 36 and a control device 37.

The actuator 33 is operated according to an instruction provided to the drive unit 32 by a slave control unit 52 which will be described later and an instruction from the control device 37. The actuator 33 generates power for operating the end effector 13 and the elongated portion 14. The power generated by the actuator 33 is transmitted to the second transmission unit 38.

The first encoder 34 is connected to the control device 37 and the slave control unit 52 to detect a rotation amount of the actuator 33.

The deceleration mechanism 35 has, for example, a plurality of gears and is connected to the actuator 33 and the second transmission unit 38 to reduce the power generated by the actuator 33 and then transmit reduced power to the second transmission unit 38.

The second encoder 36 is installed on a second rotating body 39 of the second transmission unit 38, which will be described later, to detect a rotation amount of the second rotating body 39.

The control device 37 is connected to the first encoder 34 and the second encoder 36. Further, the control device 37 controls an operation of the actuator 33 to rotate the actuator 33 on the basis of a difference between the rotation amount detected by the first encoder 34 and the rotation amount detected by the second encoder 36.

The medical manipulator 1 according to the embodiment actively operates the second rotating body 39 using information of the rotation amount detected by the first encoder 34 and the second encoder 36 during an installation process of the first base end portion 20 on the motor unit 30 (the second base end portion).

Also, instead of the second encoder 36, a torque sensor which is not illustrated may be provided. In this case, the torque sensor detects a torque with which the engaging thread portion 27 (the protruding portion 26) provided at the first rotating body 23 rotates the second rotating body 39 and thus causes the controller 50 to specify a direction in which the second rotating body 39 is to be rotated. Further, when a potentiometer which is not illustrated is provided instead of the torque sensor, the same advantage can also be obtained.

As illustrated in FIG. 7, the second transmission unit 38 includes the second rotating body 39 and the engaged portion 42.

The second rotating body 39 is a bar-shaped member which is rotatable by receiving the power generated by the actuator 33 of the drive unit 32. The second rotating body 39 is connected to the second housing 31 to be rotatable about a predetermined rotation center X2. A rotation center of the second rotating body 39 is coaxial with the rotation center of the first rotating body 23 in a state in which the first base end portion 20 is installed on the motor unit 30 (the second base end portion). The number of the second rotating bodies 39 is set to a number corresponding to the number of the first rotating bodies 23. The number of the second rotating bodies 39 of the embodiment is the same as that of the first rotating bodies 23, and all of the second rotating bodies 39 are disposed in the second housing 31.

A center line of the second rotating body 39 of the embodiment is a predetermined rotation center X2 of the second rotating body 39. Further, a first end 40 of both ends 40 and 41 of the second rotating body 39 in the center line direction is connected to the drive unit 32.

As illustrated in FIGS. 7, 10 and 11, the engaged portion 42 is provided at the second end 41 on a side opposite to the first end 40 of both ends 40 and 41 of the second rotating body 39 in the center line direction. The engaged portion 42 is integrally rotatable with the second rotating body 39 about the predetermined rotation center X2 (the center line of the second rotating body 39 in the embodiment) of the second rotating body 39. In the embodiment, the engaged portion 42 and the second rotating body 39 are integrally molded. Also, the engaged portion 42 and the second rotating body 39 may be separate bodies and may be connected to each other.

The engaged portion 42 in the embodiment has a groove portion 43 which is long in a direction orthogonal to the predetermined rotation center X2 of the second rotating body 39. The groove portion 43 has a shape based on a shape of the protruding portion 26 to be engaged with the protruding portion 26 when in a predetermined positional relationship with the engaging thread portion 27 of the protruding portion 26.

The groove portion 43 has a tapered surface 44 with which the engaging thread portion 27 of the protruding portion 26 is capable of coming in contact. The second rotating body 39 is able to be smoothly rotated by the tapered surface 44 so that a direction of the groove portion 43 follows a direction of the engaging thread portion 27 of the protruding portion 26. The tapered surface 44 provided at the groove portion 43 expands toward the engaging thread portion 27 so that the engaging thread portion 27 is inserted into the groove portion 43 even when the direction of the groove portion 43 and the direction of the engaging thread portion 27 deviate from each other within a predetermined allowable range. Also, the tapered surface 44 has a V-shaped structure which gradually narrows toward the first end 40 of the second rotating body 39 so that the groove portion 43 moves to follow the direction of the engaging thread portion 27 by pressing the engaging thread portion 27 into the groove portion 43.

The treatment tool installation sensor 45 is constituted by, for example, a light sensor or the like. When the first base end portion 20 is spaced apart from the motor unit 30 (the second base end portion) by a predetermined distance or more, the treatment tool installation sensor 45 can generate a signal which causes the controller 50 to determine that installation of the first base end portion 20 on the motor unit 30 (the second base end portion) can be performed. Further, the treatment tool installation sensor 45 may be a contact sensor which is switched on and off according to a distance between the first base end portion 20 and the motor unit 30 (the second base end portion). A specific constitution of the treatment tool installation sensor 45 and a detection procedure of an installation/separation state are not particularly limited.

The slave arm 49 illustrated in FIG. 1 is an articulated robot to which the motor unit 30 (the second base end portion) is installed. The slave arm 49 is operated in response to an instruction provided by the slave control unit 52 on the basis of an operation of the operator on the master manipulator 2.

As illustrated in FIG. 3, the controller 50 illustrated in FIG. 1 includes the master control unit 51, the slave control unit 52 and a mode control unit 53.

Each of encoders of the master arm 3 outputs information on the basis of an operation of the master manipulator 2 on the master arm 3. The master control unit 51 receives the information output from each of the encoders of the master arm 3. The master control unit 51 receives the operation of the operator on the master arm 3 on the basis of the received information, generates a predetermined instruction for operating the slave control unit 52 and outputs the instruction to the slave control unit 52. A constitution of the master control unit 51 is not particularly limited, and a well-known operation flow may be appropriately applied.

The slave control unit 52 operates the slave arm 49 and the treatment tool 12 on the basis of the above-described predetermined instruction generated by the master control unit 51 and output to the slave control unit 51. That is, the slave control unit 52 provides an instruction to the slave arm 49 and the treatment tool 12.

The mode control unit 53 performs switching between a target value control mode (a first mode) and an assist control mode (a second mode). The target value control mode (the first mode) is a mode in which the treatment tool 12 is used in a state in which the first base end portion 20 is installed on the motor unit 30 (the second base end portion). The assist control mode (the second mode) is a mode in which the first base end portion 20 is installed on and separated from the motor unit 30 (the second base end portion).

The target value control mode is a mode for providing a predetermined instruction to the drive unit 32 to operate the treatment tool 12 in response to an operation input to the master arm 3. In the target value control mode, the operation input to the master arm 3 defines an operation target value of the drive unit 32.

The assist control mode is a mode in which the drive unit 32 is operated in an installation process of the first base end portion 20 on the motor unit 30 (the second base end portion).

Figure 12:
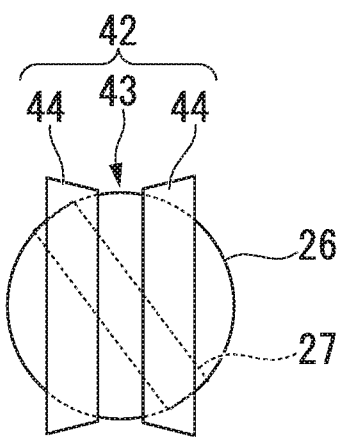
FIG. 12 is a schematic view illustrating a state before engagement of the engaged portion with the protruding portion of the medical manipulator according to the first embodiment.
Figure 13:
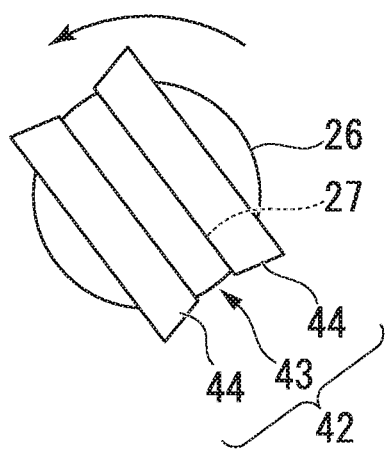
FIG. 13 is a schematic view illustrating an engagement operation of the engaged portion with the protruding portion of the medical manipulator according to the first embodiment.

An operation of the motor unit (the second base end portion) in the assist control mode will be described. FIG. 12 is a schematic view illustrating a state before engagement of the engaged portion 42 with the protruding portion 26. FIG. 13 is a schematic view illustrating an engagement operation of the engaged portion 42 with the protruding portion 26.

In the assist control mode, the controller 50 (refer to FIG. 3) does not output an instruction for operating the drive unit 32 according to an input operation to the master arm 3.

In the assist control mode, when there is a difference between the rotation amount detected by the first encoder 34 (refer to FIG. 7) and the rotation amount detected by the second encoder 36, the controller 50 operates the actuator 33 in a direction of eliminating the difference in the rotation amount.

When the engaging thread portion 27 (the protruding portion 26) is engaged with the engaged portion 42 under the assist control mode, the engaged portion 42 is pressed and rotated by the engaging thread portion 27 to be in the predetermined positional relationship based on the shape of the engaging thread portion 27 in an engaging process with the engaging thread portion 27. Also, the second rotating body 39 is rotated by a force for the control device 37 to rotate the second rotating body 39 using the actuator 39 under control of the controller 50 in addition to a force for the engaging thread portion 27 to press the engaged portion 42 and rotate the second rotating body 39.

In the embodiment, the controller 50 controls the drive unit 32 to cause the second rotating body 39 to perform a following operation (an assisting operation) in a rotation direction of the second rotating body 39 which is specified by the difference between the rotation amount of the first encoder 34 and the rotation amount of the second encoder 36. Accordingly, a state in which a direction of the engaged portion 42 does not coincide with that of the engaging thread portion 27 (FIG. 12) is changed to a state in which the engaged portion 42 is positioned following the direction of the engaging thread portion 27 (FIG. 13). As a result, in the embodiment, a load on the second rotating body 39 and the drive unit 32 in the installation process of the first base end portion 20 on the motor unit 30 (the second base end portion) is low.

Further, in the embodiment, even when the deceleration mechanism 35 such as a gear is disposed in a power transmission path from the actuator 33 of the drive unit 32 to the second rotating body 39, an unintended movement of the end effector 13 and the joint portion 15 in an installation and separation process of the first base end portion 20 and the motor unit 30 (the second base end portion) can be reduced.

Figure 14:
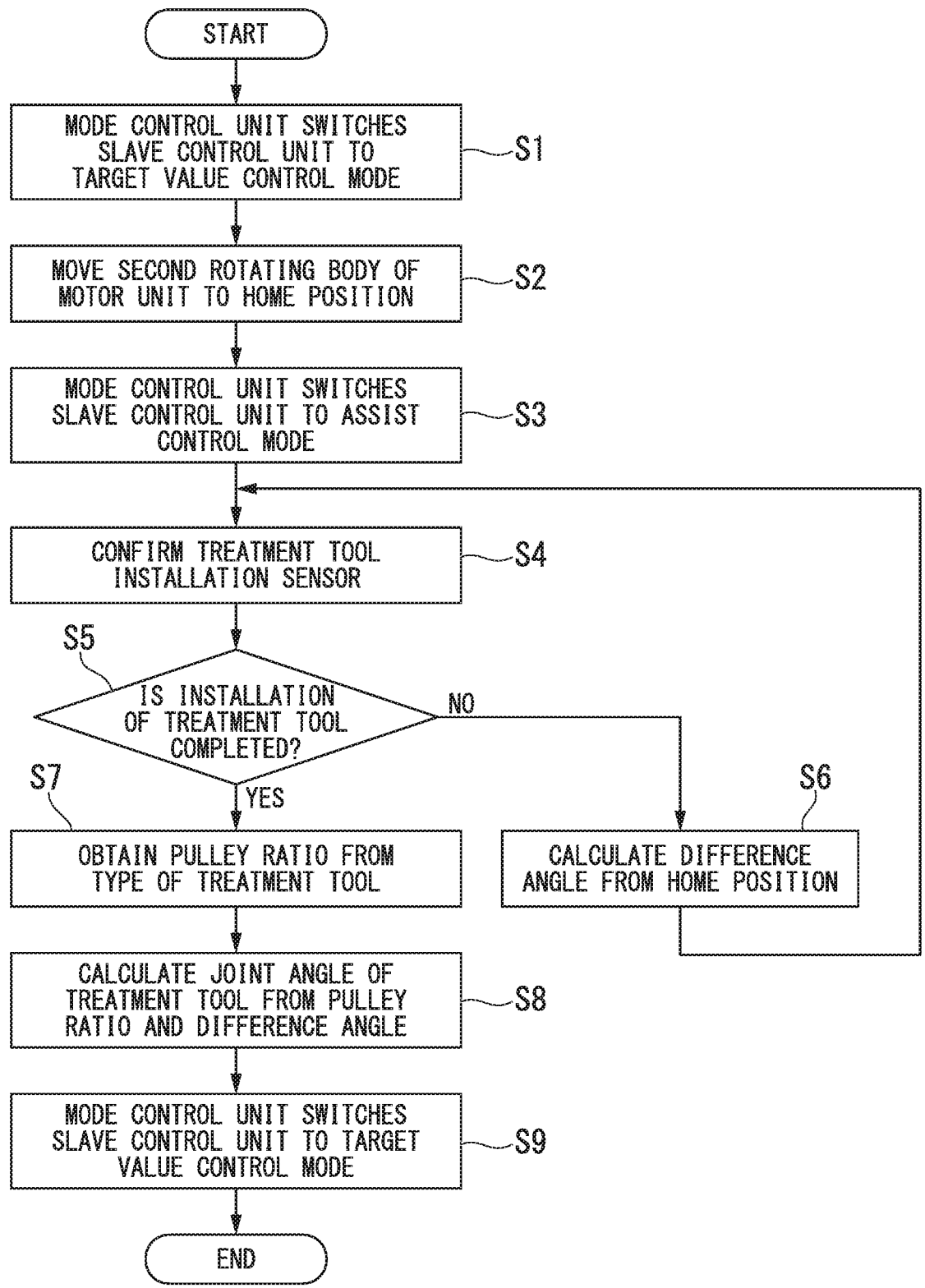
FIG. 14 is a flowchart illustrating an operation of the medical manipulator according to the first embodiment.
Figure 15:
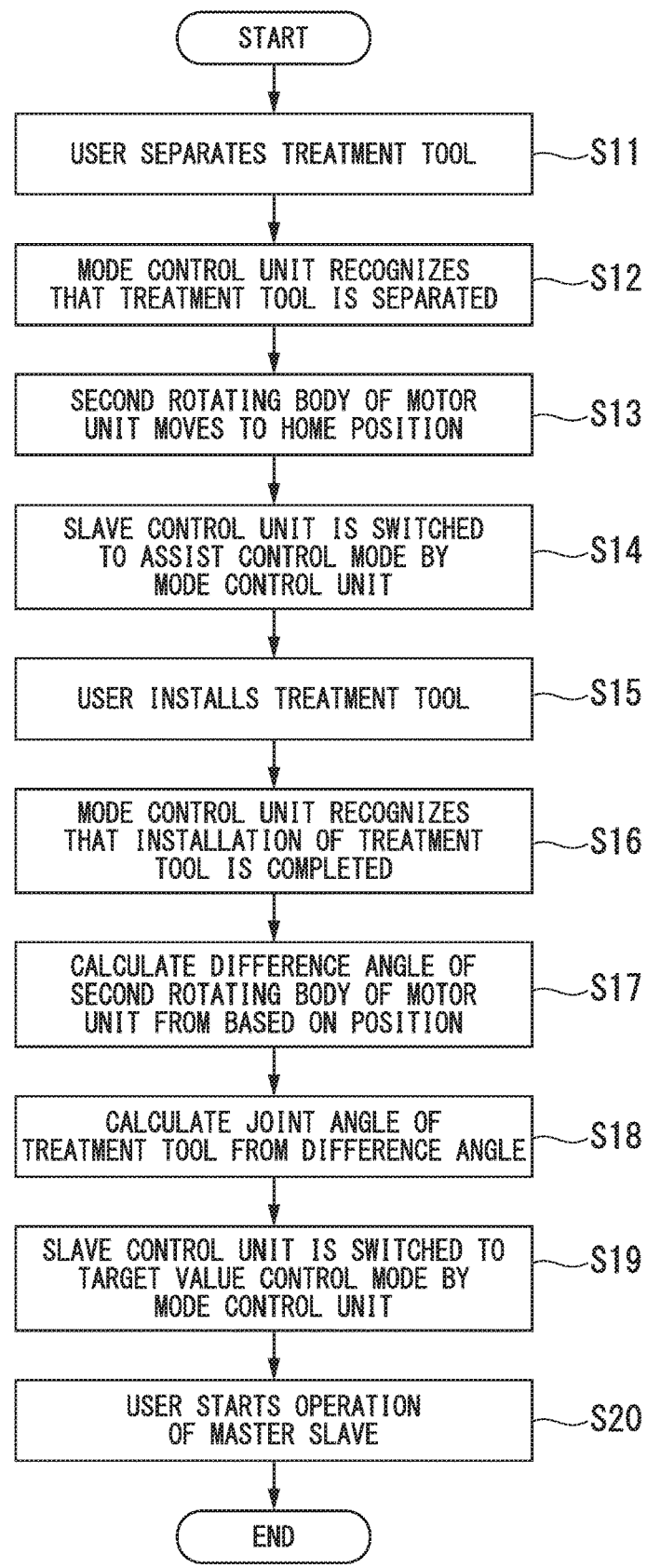
FIG. 15 is a flowchart illustrating a process in which the treatment tool is installed on and separated from the motor unit of the medical manipulator according to the first embodiment.

An operation of the medical manipulator 1 according to the embodiment will be described. FIG. 14 is a flowchart illustrating an operation of the medical manipulator. FIG. 15 is a flowchart illustrating a process in which the treatment tool is installed on and separated from the motor unit of the medical manipulator.

First, an operation flow from activation of the medical manipulator 1 to start of use of the treatment tool 12 will be exemplified.

First, the medical manipulator 1 according to the embodiment is activated. In the embodiment, the first base end portion 20 of the treatment tool 12 may be installed on the motor unit 30 (the second base end portion) before activation of the medical manipulator 1, or the first base end portion 20 of the treatment tool 12 may not be installed on the motor unit 30 (the second base end portion) when the medical manipulator 1 is activated. Hereinafter, the operation flow in a case in which the first base end portion 20 of the treatment tool 12 is not installed on the motor unit 30 (the second base end portion) when the medical manipulator 1 is activated will be exemplified.

After the medical manipulator 1 is activated, the mode control unit 53 switches the slave control unit 52 to the target value control mode (step S1) and operates the drive unit 32 to be in a predetermined initial state (a home position) (step S2).

If the first base end portion 20 is installed on the motor unit 30 (the second base end portion) in step S2, the second rotating body 39 is located at the home position, and thus the treatment tool 12 also has a position and a posture corresponding to the home position.

After step S2, the mode control unit 53 switches the slave control unit 52 to the assist control mode (step S3).

After step S3, the controller 50 confirms a detection state of the treatment tool installation sensor 45 (step S4), and when it is determined in the treatment tool installation sensor 45 that the first base end portion 20 is not installed on the motor unit 30 (No in step S5), a difference angle of the current second rotating body 39 based on the home position of the second rotating body 39 is calculated, and the process returns to step S4 (step S6). When the first base end portion 20 of the treatment tool 12 is installed on the motor unit 30 while each of steps S4 to S6 is repeated, the latest difference angle is calculated in step S6 which is repeatedly executed.

Further, in a process from step S4 to step S6 while the mode is switched to the assist control mode, the controller 50 does not output an instruction for operating the drive unit 32 according to the input operation to the master arm 3. In the assist control mode, the controller 50 operates the actuator 33 in a direction of eliminating the difference in the rotation amount using the control device 37 when there is a difference between the rotation amount of the first encoder 34 and the rotation amount of the second encoder 36.

When the first base end portion 20 of the treatment tool 12 is installed on the motor unit 30 while each of steps S4 to S6 is repeated, the first rotating body 23 provided at the first base end portion 20 and the engaging thread portion 27 (the protruding portion 26) thereof move the second rotating body 39 and the drive unit 32 so that the engaging thread portion 27 (the protruding portion 26) is engaged with the groove portion 43 (the engaged portion 42).

In the treatment tool installation sensor 45, when it is determined that the first base end portion 20 is installed on the motor unit 30 (Yes in step S5), a pulley ratio corresponding to a type of the treatment tool 12 is obtained in a state having information of the latest difference angle (step S7). The pulley ratio in the embodiment is a unique value for each type of the treatment tool 12 and defines a bending angle of the joint element 16 of the treatment tool 12 with respect to a rotation angle of the first rotating body 23. For example, the operator instructs the type of the treatment tool 12 from the master manipulator 2 to the controller 50. Accordingly, the controller 50 can acquire the pulley ratio which is the basis of the relationship between a driving amount of the drive unit 32 and the operation amount of the end effector 13 and the joint portion 15 of the treatment tool 12.

After step S7, a position and a posture of the end effector 13 and the joint portion 15 at the present time point are calculated based on the difference angle of the second rotating body 39 detected in step S6 and the pulley ratio based on the type of the treatment tool 12 obtained in step S7 (step S8).

After step S8, the mode control unit 53 switches the slave control unit 52 from the assist control mode to the target value control mode (step S9).

An operation by the master arm 3 of the master manipulator 2 can be accepted as the position and posture of the end effector 13 and the joint portion 15 calculated in step S8 according to a flow from step S1 to step S9 as the current position and posture. That is, from termination of step S9, it is possible to use the treatment tool 12 using the master manipulator 2.

Next, an operation flow of the assist control mode in a process in which the treatment tool 12 is replaced with another treatment tool 12 in a state in which the first base end portion 20 is installed on the motor unit 30 (the second base end portion) in advance and the treatment tool 12 is used will be exemplified.

As illustrated in FIG. 15, first, a user of the medical manipulator 1 separates the first base end portion 20 from the motor unit 30 (the second base end portion), for example, manually (step S11).

In step S11, the engaging thread portion 27 of the protruding portion 26 is removed from the groove portion 43 of the engaged portion 42, and thus power transmission from the second transmission unit 38 to the first transmission unit 22 is disabled. Since the first rotating body 23 of the first transmission unit 22 does not rotate in the first housing 21 but is held in the first housing 21, the end effector 13 and the joint portion 15 do not operate in a separation process of the first base end portion 20 from the motor unit 30 (the second base end portion). This completes step S11 and the process then proceeds to step S12.

Step 12 is a step in which the mode control unit 53 recognizes that the treatment tool 12 is disengaged in response to separation of the first base end portion 20 from the motor unit 30 in step S11. In step S12, for example, the mode control unit 53 referring to the treatment tool installation sensor 45 determines that the treatment tool 12 is separated from the motor unit 30 in response to movement of the first base end portion 20 out of a detection limit of the treatment tool installation sensor 45.

This completes step S12 and the process then proceeds to step S13.

In step S13, the slave control unit 52 moves the second rotating body 39 of the motor unit 30 to the home position. The motor unit 30 is initialized (returned to the home position) by the movement of the second rotating body 39 to the home position.

This completes step S13 and the process then proceeds to step S14.

In step S14, the slave control unit 52 is switched to the assist control mode by the mode control unit 53. As the slave control unit 52 is switched from the target value control mode to the assist control mode in step S14, the second rotating body 39 of the motor unit 30 is rotatable according to an installation operation of the first base end portion 20.

This completes step S14 and the process then proceeds to step S15.

Step S15 is a step in which the operator installs the first base end portion 20 of a new treatment tool 12 on the motor unit 30 (the second base end portion).

In step S15, first, the operator installs the new treatment tool 12 on the first lumen 9 or the second lumen 10 so that the end effector 13 and the joint portion 15 of the new treatment tool 12 protrude from a tip end of the medical overtube 8 by a predetermined length. For example, when the medical overtube 8 is curved, a path length of the drive wire W2, the angle wire W1 or the like disposed in the flexible tube portion 17 of the treatment tool 12 may be changed according to a curved shape of the medical overtube 8. Furthermore, a state of the drive wire W2 and the angle wire W1 may be changed according to a state of the end effector 13 and the joint portion 15 protruding from the tip end of the medical overtube 8. Accordingly, for example, even if the end effector 13 is located at a predetermined initial position and the elongated portion 14 in a linear state is regarded as the initial position, the first transmission unit 22 provided at the first base end portion 20 of the new treatment tool 12 may be in a position other than the initial position immediately after the treatment tool 12 is installed in the medical overtube 8.

In addition, after the treatment tool 12 is installed in the medical overtube 8 so that the end effector 13 and the joint portion 15 of the new treatment tool 12 protrude from the tip end of the medical overtube 8 by a predetermined length, the operator may perform an adjustment by rotating the engaging thread portion 27 manually to make the joint portion 15 of the treatment tool 12 into a desired curved shape.

That is, a direction of the engaging thread portion 27 in the first housing 21 varies according to conditions such as the curved shape of the medical overtube 8 in the body and the manual adjustment by the operator.

In the embodiment, in step S15, the first housing 21 is installed in the second housing 31 after the new treatment tool 12 is installed in the medical overtube 8. The protruding portion 26 (the engaging thread portion 27) of the first rotating body 23 connected to the first housing 21 is inserted into the engaged portion 42 (the groove portion 43) of the second rotating body 39 connected to the second housing 31, and the engaging thread portion 27 comes in contact with the tapered surface 44 of the groove portion 43 and rotates the second rotating body 39. When a predetermined positional relationship in which the engaging thread portion 27 and the groove portion 43 are in the same direction is satisfied, the engaging thread portion 27 is completely engaged with the groove portion 43.

In step S15, the first rotating body 23 having the engaging thread portion 27 does not rotate in the first housing 21 but rotates the second rotating body 39, and thus the first base end portion 20 and the motor unit 30 (the second base end portion) can be properly installed. Therefore, in the installation process of the first base end portion 20 in the motor unit 30 (the second base end portion) in step S15, the end effector 13 and the joint portion 15 of the treatment tool 12 do not operate.

This completes step S15 and the process then proceeds to step S16.

Step S16 is a step in which the mode control unit 53 recognizes that the installation of the treatment tool 12 is completed. In step S16, for example, when the treatment tool installation sensor 45 recognizes the first base end portion 20 at a predetermined position, the mode control unit 53 can determine that the installation of the treatment tool 12 is completed.

This completes step S16 and the process then proceeds to step S17.

In step S17, the difference angle of the current second rotating body 39 based on the home position of the second rotating body 39 of the motor unit 30 is calculated.

This completes step S17 and the process then proceeds to step S18.

Step S18 is a step in which the state of the end effector 13 and the joint portion 15 in the treatment tool 12 newly installed in the motor unit 30 (the second base end portion) is obtained.

In step S18, for example, the operator instructs the controller 50 via the master manipulator 2 about information specifying the type of the treatment tool 12 installed in the motor unit 30 (the second base end portion). Then, the controller 50 calculates the position and posture of the end effector 13 and the joint portion 15 protruding from the tip end of the medical overtube 8 on the basis of information of parameters stored in advance corresponding to the type of the treatment tool 12 and the position of the second rotating body 39. For example, the controller 50 calculates an angle of the joint portion 15 of the treatment tool 12 from the difference angle calculated in the above-described step S17.

This completes step S18 and the process then proceeds to step S19.

Step S19 is a step of making the treatment tool 12 usable by switching the assist control mode to the target value control mode.

In step S19, the controller 50 recognizes the current position and posture of the end effector 13 and the joint portion 15 on the basis of the parameter indicating the angle of the joint portion 15 or the like and allows an instruction for operating the drive unit 32 to be output to the drive unit 32 of the treatment tool 12 in response to the operator's operation on the master arm 3 of the master manipulator 2.

This completes step S19, and then the operator (the user) can start a master-slave operation of the medical manipulator 1 in the target value control mode (step S20). Further, when it is necessary to further replace the treatment tool 12 while the medical manipulator 1 is used in the target value control mode, it is possible to replace the treatment tool 12 with still another treatment tool 12 through the above-described steps S11 to S19.

According to the medical manipulator 1 of the embodiment as described above, when the first base end portion 20 of the new treatment tool 12 is installed on the motor unit 30 (the second base end portion), the second rotating body 39 rotates until the second rotating body 39 on the motor unit 30 (the second base end portion) side is engaged with the first rotating body 23 in a predetermined positional relationship even though the first base end portion 20 is installed on the motor unit 30 (the second base end portion) without confirming the positional relationship between the first rotating body 23 and the second rotating body 39. Accordingly, when the first base end portion 20 of the new treatment tool 12 is installed on the motor unit 30 (the second base end portion), the end effector 13 and the joint portion 15 of the new treatment tool 12 do not operate. As a result, according to the medical manipulator 1 of the embodiment, the unintended movement of the end effector 13 and the joint portion 15 in the installation and separation process of the first base end portion 20 and the motor unit 30 (the second base end portion) can be reduced.

Further, since the groove portion 43 of the engaged portion 42 has the tapered surface 44 which can come in contact with the engaging thread portion 27 of the protruding portion 26, a force with which the protruding portion 26 is pressed against the groove portion 43 is converted into a rotational force of the second rotating body 39. As a result, even when the direction of the engaging thread portion 27 and the direction of the groove portion 43 are different from each other, the direction of the groove portion 43 can be changed following the direction of the engaging thread portion 27 due to the installation operation of the first base end portion 20 on the motor unit 30 (the second base end portion).

MODIFIED EXAMPLE 1

Figure 16:
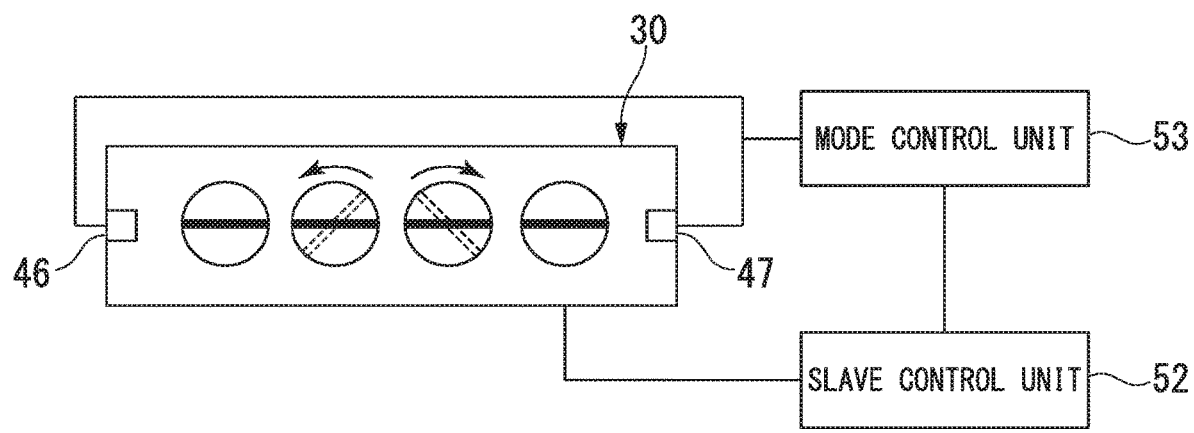
FIG. 16 is a schematic view illustrating a constitution of the motor unit in a modified example of the medical manipulator according to the first embodiment.
Figure 17:
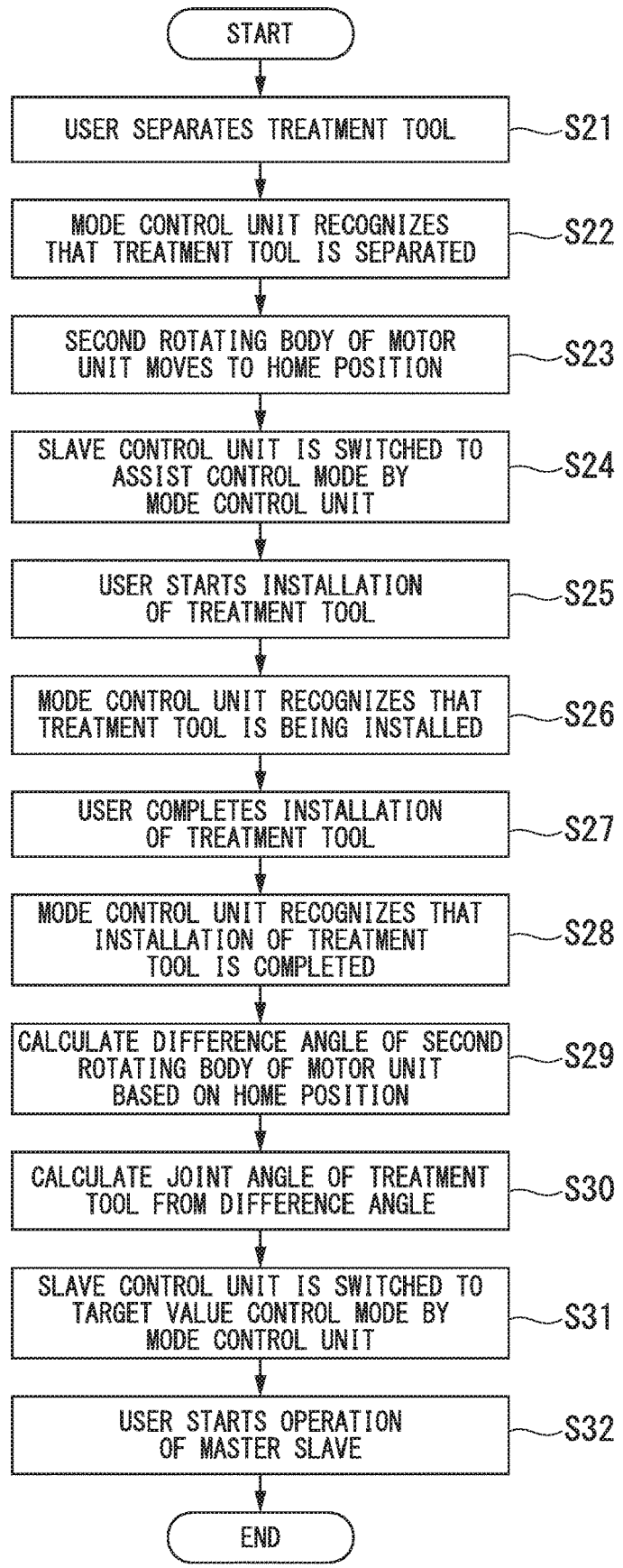
FIG. 17 is a flowchart illustrating an operation in the modified example of the medical manipulator according to the first embodiment.

A modified example of the medical manipulator according to the embodiment will be described. FIG. 16 is a schematic view illustrating a constitution of the motor unit in a modified example. FIG. 17 is a flowchart illustrating an operation of the medical manipulator according to the modified example.

In the modified example, as illustrated in FIG. 16, instead of the treatment tool installation sensor 45 disclosed in the first embodiment, an installation/separation process detecting sensor 46 and an installation completion detecting sensor 47 are provided.

Both of the installation/separation process detecting sensor 46 and the installation completion detecting sensor 47 are connected to the mode control unit 53.

The installation/separation process detecting sensor 46 is a sensor which detects a process in which the first base end portion 20 (for example, refer to FIG. 4) of the treatment tool 12 is installed on and separated from the motor unit 30 (the second base end portion). The installation/separation process detecting sensor 46 has, for example, a magnetic sensor. The installation/separation process detecting sensor 46 detects the movement of the first base end portion 20 with respect to the motor unit 30 and thus causes the mode control unit 53 to recognize the installation and separation operation of the first base end portion 20 on the motor unit 30.

The installation completion detecting sensor 47 is a sensor which detects completion of the installation process of the first base end portion 20 (for example, refer to FIG. 4) on the motor unit 30. The installation completion detecting sensor 47 has, for example, a photo sensor. The installation completion detecting sensor 47 detects whether or not the motor unit 30 and the first base end portion 20 are in a predetermined positional relationship in which the first base end portion 20 is installed on the motor unit 30 and thus causes the mode control unit 53 to recognize whether or not the installation of the first base end portion 20 on the motor unit 30 is completed.

A replacement operation of the treatment tool 12 in the modified example will be described with reference to FIG. 17.

In the modified example, like steps S11 to S14 in the first embodiment, the user separates the treatment tool 12, whereby the slave control unit 52 is switched to the assist control mode (steps S21 to S24).

In a state in which the assist control mode is set in the above-described step 24, the user starts an operation in which the new treatment tool 12 is installed on the motor unit 30 (step S25).

After step S25, the user brings the first base end portion 20 close to the motor unit 30 to install the treatment tool 12 on the motor unit 30. Then, the installation/separation process detecting sensor 46 detects the fact that the first base end portion 20 is installed on or separated from the motor unit 30. When the user brings the first base end portion 20 close to the motor unit 30, the mode control unit 53 recognizes the fact that the treatment tool 12 is installed on the basis of a detection state of the installation/separation process detecting sensor 46 (step S26).

After step S26, the user completes the installation operation of the treatment tool 12 on the motor unit 30 (step S27). After step 27, the installation completion detecting sensor 47 detects whether or not the first base end portion 20 is correctly installed on the motor unit 30 with the predetermined positional relationship. The mode control unit 53 recognizes the fact that the user has completed the operation of bringing the first base end 20 close to the motor unit 30 on the basis of the detection state of the installation completion detecting sensor 47 (step S28).

After Step S28, like steps S17 to S19 in the first embodiment, the difference angle of the current second rotating body 39 based on the home position of the second rotating body 39 of the motor unit 30 is calculated (Step S29), the controller 50 calculates the angle of the joint portion 15 of the treatment tool 12 from the difference angle on the basis of a calculated result (step S30), the assist control mode is switched to the target value control mode (step S31), and thus the treatment tool 12 can be used.

After completion of step S31, the user can start the master-slave operation of the medical manipulator 1 in the target value control mode (step S32).

A constitution of the modified example also has the same effects as those in the first embodiment. Further, in the modified example, the installation/separation process detecting sensor 46 for detecting the installation process of the treatment tool 12 on the motor unit 30 and the installation completion detecting sensor 47 for detecting whether or not the treatment tool 12 is correctly installed on the motor unit 30 perform the detection operation independently.

MODIFIED EXAMPLE 2

Figure 18:
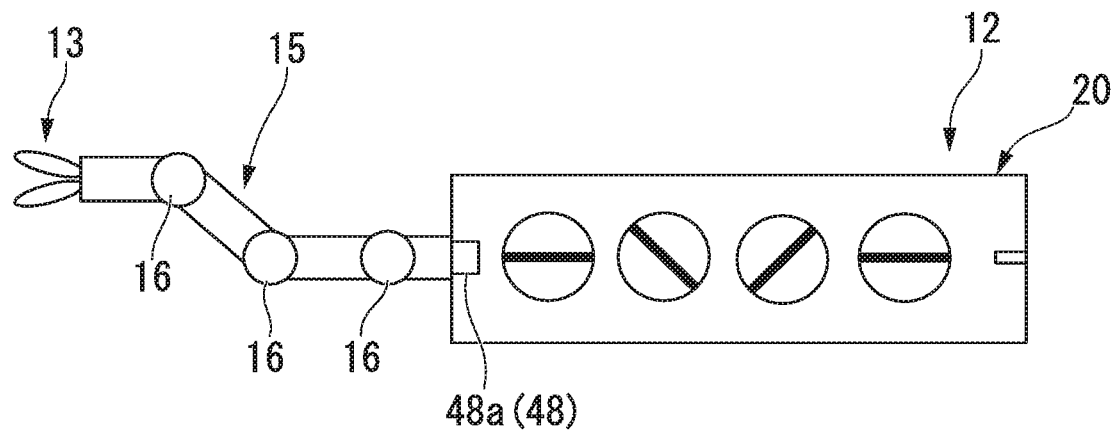
FIG. 18 is a schematic view illustrating a constitution of the treatment tool in another modified example of the medical manipulator according to the first embodiment.
Figure 19:
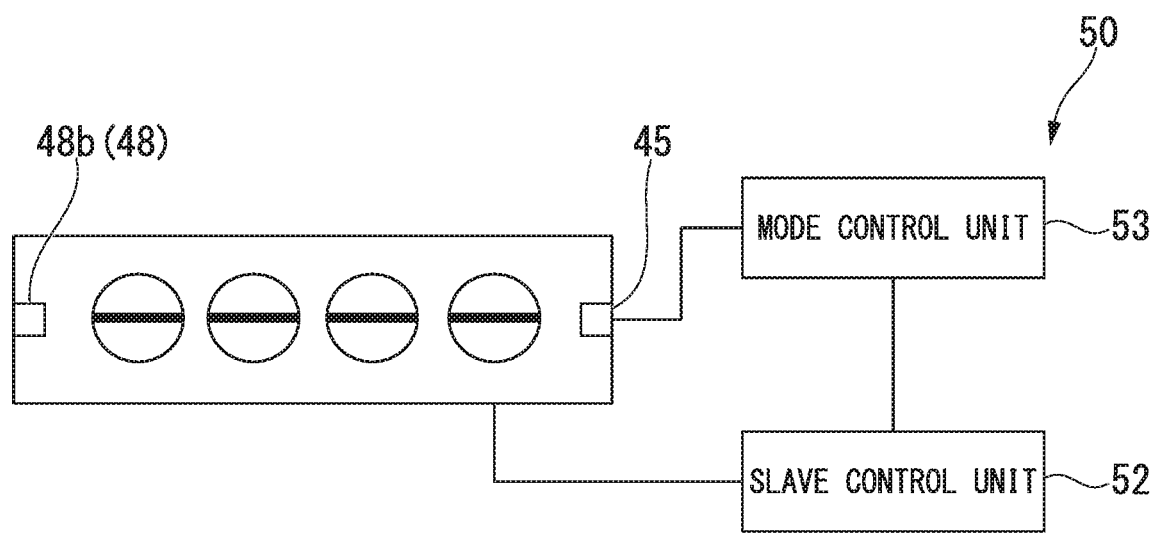
FIG. 19 is a schematic view illustrating a constitution of the motor unit in another modified example of the medical manipulator according to the first embodiment.

A modified example of the medical manipulator according to the embodiment will be described. FIG. 18 is a schematic view illustrating a constitution of the treatment tool in the modified example. FIG. 19 is a schematic view illustrating a constitution of the motor unit in the modified example.

As illustrated in FIGS. 18 and 19, the medical manipulator 1 of the modified example further includes an identification sensor 48 which causes the controller 50 to acquire information specifying the type of the treatment tool 12 installed on the motor unit 30 (the second base end portion) in addition to the treatment tool installation sensor 45 disclosed in the first embodiment.

The identification sensor 48 may be constituted to have a unique ID 48a for each type of the treatment tool 12 provided at the first base end portion 20 and a recognition part 48b for recognizing the ID provided on the motor unit 30 (the second base end portion). The identification sensor 48 may be a contact type or a non-contact type.

Also, the identification sensor 48 may be an electronic type which reads the electronically encoded ID or may be a mechanical type including a switch group which reads a predetermined shape corresponding to the type of the treatment tool 12.

In the modified example, the switching between the target value control mode and the assist control mode is automatically performed by the controller 50 on the basis of presence or absence of an installation signal in the treatment tool installation sensor 45. That is, in the modified example, when the first base end portion 20 is separated from the motor unit 30 (the second base end portion), the switching to the assist control mode disclosed in the first embodiment is performed.

Furthermore, in the modified example, the type of the new treatment tool 12 including the first base end portion 20 newly installed on the motor unit 30 (the second base end portion) is specified automatically by the controller 50 on the basis of information obtained by the identification sensor 48. Further, the controller 50 can automatically recognize the position and posture of the end effector 13 or the joint portion 15 of the treatment tool 12 or both of the end effector 13 and the joint portion 15 based on the information obtained by the identification sensor 48.

Second Embodiment

Figure 20:
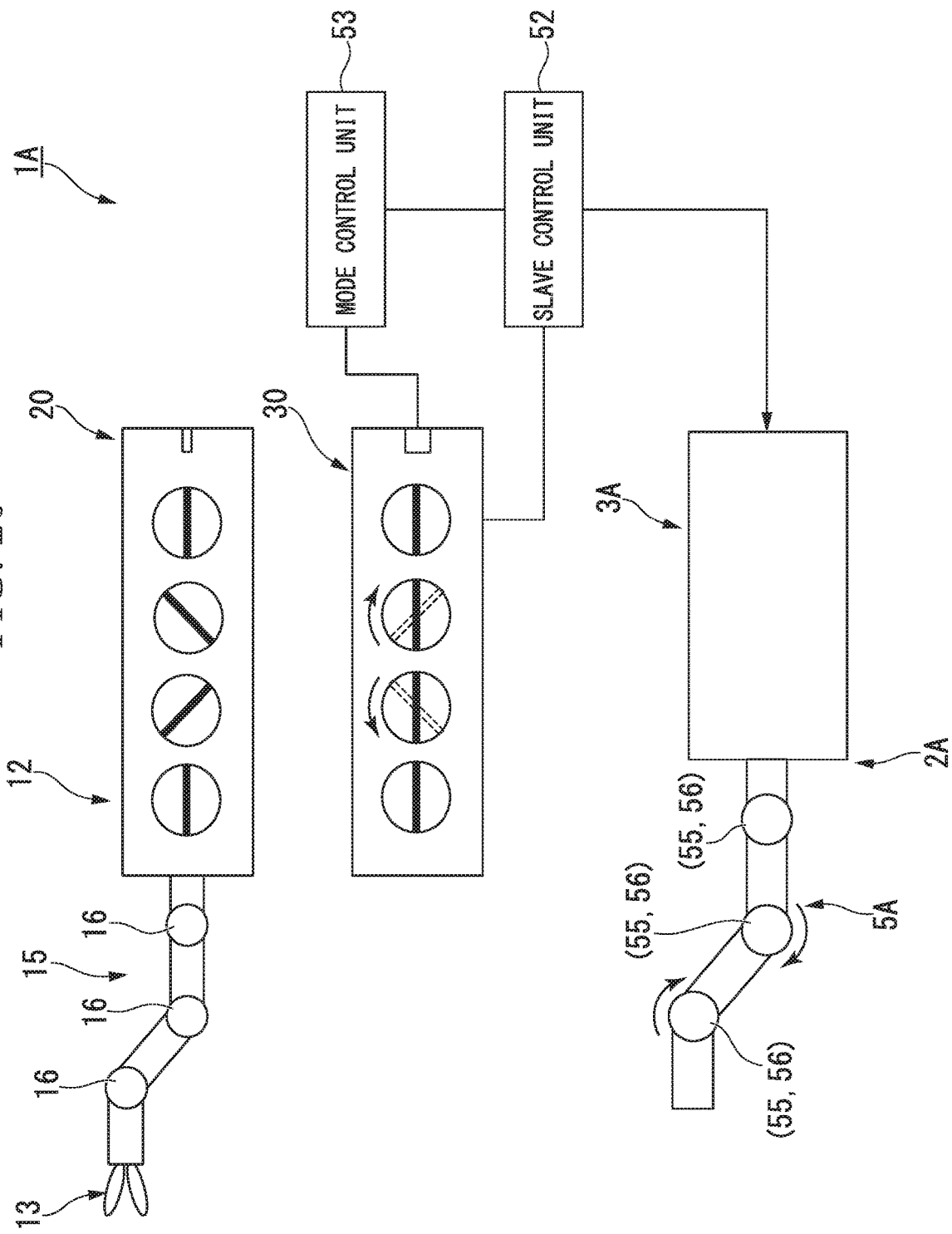
FIG. 20 is a schematic view illustrating a constitution of a part of a medical manipulator according to a second embodiment.

A second embodiment will be described. FIG. 20 is a schematic view illustrating a constitution of a part of a medical manipulator according to a second embodiment of the present invention. In the embodiment, the same elements as those disclosed in the first embodiment are denoted by the same reference signs as those in the first embodiment, and descriptions overlapping with the first embodiment are omitted.

A medical manipulator 1A according to the embodiment illustrated in FIG. 20 includes a master manipulator 2A having a master arm 3A which is operated according to an instruction provided from the controller 50, instead of the master manipulator 2 of the first embodiment.

The master manipulator 2A of the embodiment has an articulated arm 5A which is operated according to an instruction from the controller 50, instead of the articulated arm 5 disclosed in the first embodiment.

The articulated arm 5A of the embodiment includes an actuator 55 and an encoder 56 which are connected to the controller 50.

In the medical manipulator 1A according to the embodiment, like the first embodiment, the end effector 13 and the joint portion 15 of the treatment tool 12 remain stationary while maintaining the position and posture in a protruding state from the tip end of the overtube 8 (refer to FIG. 2) during a period from the start of installation of the first base end portion 20 on the motor unit 30 (the second base end portion) to the completion of installation.

In a state in which the first base end portion 20 is installed on the motor unit 30 (the second base end portion), the position and posture of the end effector 13 and the joint portion 15 of the newly installed treatment tool 12 are independent of a shape of the master arm 3A of the master manipulator 2A.

The controller 50 in the embodiment reflects the position and posture of the end effector 13, the joint portion 15 of the newly installed treatment tool 12 or both of them in the shape of the master arm 3A of the master manipulator 2A at a certain point in time until the switching from the assist control mode to the target value control mode after the start of the assist control mode. Specifically, the controller 50 operates the actuator 55 of the master arm 3A, for example, on the basis of the rotation amount of the second rotating body 39 in the installation process of the first base end portion 20 on the motor unit (the second base end portion) and deforms the master arm 3A so that the master arm 3A has a shape similar to that of the end effector 13 and the joint portion 15.

In the embodiment, when the first base end portion 20 is installed on the motor unit 30 (the second base end portion) and the switching from the assist control mode to the target value control mode is performed, a state in which the master arm 3A has a shape similar to that of each of the end effector 13 and the joint portion 15 is automatically prepared. The state in which the master arm 3A has the shape similar to that of each of the end effector 13 and the joint portion 15 is an initial state for starting the operation of the end effector 13 and the joint portion 15 using the master arm 3A. That is, in the embodiment, the master arm 3A is constituted to be automatically initialized when the assist control mode is switched to the target value control mode. As a result, it is unnecessary for the operator to manually match the shapes of the end effector 13 and the joint portion 15 with the shape of the master arm 3A, and the use of the treatment tool 12 can quickly start after the new treatment tool 12 is installed.

Although the embodiments of the present invention have been described above in detail with reference to the drawings, the specific constitution is not limited to these embodiments, and design changes or the like within the scope not departing from the gist of the present invention are included.

Figure 21:
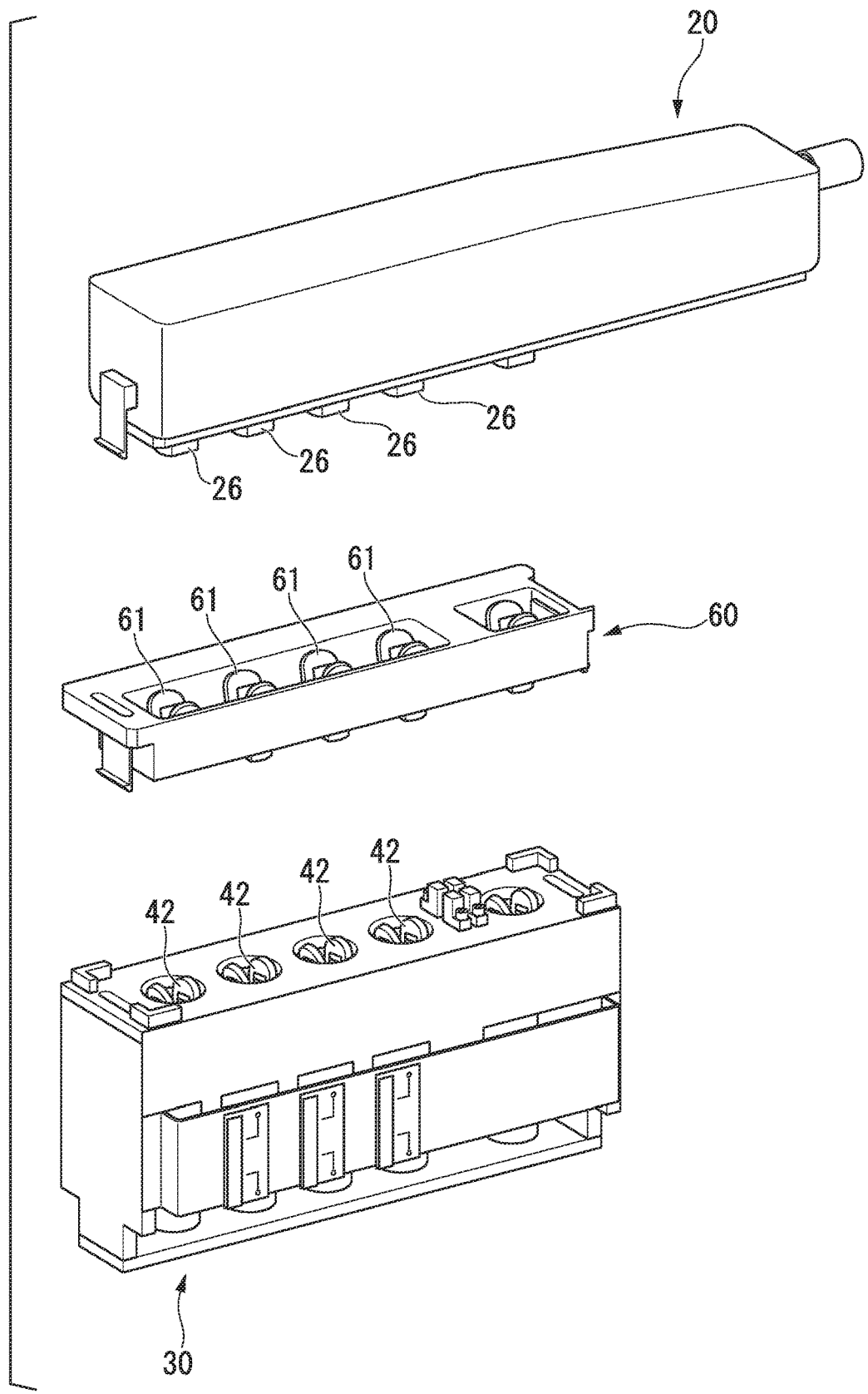
FIG. 21 is a perspective view illustrating an example of a design change in the medical manipulator according to the embodiment.

For example, as illustrated in FIG. 21, the first base end portion 20 and the motor unit 30 may be connected to each other via an intermediate member 60. The intermediate member 60 prevents the first base end portion 20 exsisting in the clean area and the motor unit 30 exsisting in the unclean area from coming in direct contact with each other and also transmits power to the first base end portion 20 from the motor unit 30. For example, the intermediate member 60 has a connecting member 61 which can be engaged with the protruding portion 26 and can also be engaged with the engaged portion 42. By having the intermediate member 60, it is possible to transmit the power in a state in which a device exsisting in the clean area and a device exsisting in the unclean area are not in direct contact with each other.

Further, the elements described in each of the above-described embodiments and each of the modified examples can be constituted by appropriately combining them.

In addition, in the above-described embodiments, the installation and separation of the first base end portion and the second base end portion has been described in a state in which the end effector 13 and the joint portion 15 protrude by a predetermined length from the tip end of the medical overtube 8, but the present invention is not limited to that state. For example, the first base end portion and the second base end portion may be installed/separated in a state in which the end effector 13 and the joint portion 15 are in the overtube 8. In this case, since a force of the joint portion 15 interfering with an inner wall of the overtube can be reduced, the durability of the treatment tool 12 can be improved.

What is claimed is:

1. A medical manipulator comprising:
   an elongated portion and an end effector coupled to the elongated portion, wherein at least one of the elongated portion and the end effector are configured to be driven to change a position and/or an orientation;
   a wire, wherein a distal end of the wire is operatively connected to the at least one of the elongated portion and the end effector to transmit a driving force to drive the at least one of the elongated portion and the end effector;
   a first rotatable body operatively connected to a proximal end of the wire, wherein the first rotatable body is configured to be rotated about a rotation axis to exert the driving force transmitted by the wire to drive the at least one of the elongated portion and the end effector; and
   a second rotatable body configured to be detachably coupled to the first rotatable body, wherein the second rotatable body is operatively connected to an actuator to be rotated by the actuator,
   wherein a shape of the first rotatable body corresponds to a shape of the second rotatable body such that as the first rotatable body and the second rotatable body are brought into contact with each other, a pressing force with which the first rotatable body is pressed against the second rotatable body is converted into a rotational force of the second rotatable body to rotate the second rotatable body into a predetermined alignment with the first rotatable body.

2. The medical manipulator according to claim 1, further comprising:
   a first housing operatively connected to the first rotatable body, wherein the first rotatable body is configured to rotate with respect to the first housing with a rotational resistance force of a predetermined magnitude,
   wherein the predetermined magnitude is set such that as the first rotatable body and the second rotatable body are brought into contact with each other, the pressing force which the first rotatable body is pressed against the second rotatable body is converted into the rotational force of the second rotatable body to rotate the second rotatable body into the predetermined alignment with the first rotatable body.

3. The medical manipulator according to claim 1, further comprising:
   the actuator;
   one or more sensors configured to detect a rotation amount of the second rotatable body and a rotation amount of the actuator; and
   a controller,
   wherein in an assist control mode, the controller is configured to perform, at least:
      determine a difference between the rotation amount of the second rotatable body and the rotation amount of the actuator; and
      control the actuator to rotate in a direction to eliminate the difference.

4. The medical manipulator according to claim 3,
   wherein the controller is configured to receive an instruction signal from a master manipulator manipulated by a user to instruct a change in the position and/or the orientation of the at least one of the elongated portion and the end effector,
   wherein in the assist control mode, the controller is configured to not control the actuator in accordance with the instruction signal, and
   wherein in a target value control mode, the controller is configured to:
      control the actuator to rotate the second rotatable body in accordance with the instruction signal, such that the second rotatable body that is coupled to the first rotatable body rotates the first rotatable body about the rotation axis to exert the driving force that is transmitted by the wire to drive the at least one of the elongated portion and the end effector.

5. The medical manipulator according to claim 1,
   wherein the first rotatable body comprises a protrusion,
   wherein the second rotatable body comprises a groove, and
   wherein as the first rotatable body and the second rotatable body are brought into contact with each other, the groove is configured to convert the pressing force with which the first rotatable body is pressed against the second rotatable body into the rotational force of the second rotatable body to rotate the second rotatable body into the predetermined alignment with the first rotatable body.

6. The medical manipulator according to claim 5,
   wherein the groove comprises a tapered surface that narrows the groove in a direction in which the pressing force is applied.

* * * * *